United States Patent [19]

Von Philipsborn et al.

[11] 4,206,117
[45] Jun. 3, 1980

[54] PYRIDINYL AMINOALKYL ETHERS

[75] Inventors: Gerda Von Philipsborn, Weinheim; Walter Boell, Dannstadt-Schauernheim; Dieter Lenke, Ludwigshafen, all of Fed. Rep. of Germany

[73] Assignee: BASF Aktiengesellschaft, Fed. Rep. of Germany

[21] Appl. No.: 885,434

[22] Filed: Mar. 10, 1978
(Under 37 CFR 1.47)

[30] Foreign Application Priority Data

Mar. 17, 1977 [DE] Fed. Rep. of Germany ....... 2711655

[51] Int. Cl.² .................... A61K 31/44; C07D 307/60
[52] U.S. Cl. .............................. 424/246; 424/248.51; 424/248.52; 424/248.55; 424/248.56; 424/248.57; 424/248.58; 424/250; 424/256; 424/258; 424/263; 424/267; 544/60; 544/61; 544/58.6; 544/124; 544/128; 544/360; 544/362; 544/363; 546/300; 546/113; 546/114; 546/116; 546/183; 546/193; 546/194; 546/281; 546/284; 546/287; 546/288; 546/299

[58] Field of Search ........ 260/287 T, 288 R, 288 CE, 260/293.57, 293.58, 293.59, 293.61, 293.68, 293.69, 294.8 R, 294.8 C, 294.8 D, 294.9, 295 R, 295 AM, 295 B, 295 F, 296 A, 296 E, 296 B, 296 H; 424/246, 248.51–248.58, 250, 256, 258, 263, 267; 544/60, 61, 124, 128, 360, 362, 363; 546/113, 114, 116, 183, 299, 300

[56] References Cited

U.S. PATENT DOCUMENTS

| | | | |
|---|---|---|---|
| 1,572,768 | 2/1926 | Callsen | 260/288 R |
| 1,881,236 | 10/1932 | Miescher et al. | 260/296 AE |
| 3,535,328 | 10/1970 | Zielinski | 260/296 AE |
| 3,998,835 | 12/1976 | Troxler et al. | 260/294.8 C |
| 4,060,601 | 11/1977 | Baldwin | 424/263 |
| 4,065,461 | 12/1977 | Ross-Petersen | 260/296 AE |
| 4,073,909 | 2/1978 | Troxler et al. | 424/258 |
| 4,113,869 | 9/1978 | Gardner | 424/258 |
| 4,115,575 | 9/1978 | Frei et al. | 424/250 |

FOREIGN PATENT DOCUMENTS 1493006 11/1977 United Kingdom .

*Primary Examiner*—Richard Raymond
*Attorney, Agent, or Firm*—Keil & Witherspoon

[57] ABSTRACT

New pyridinyl aminoalkyl ethers, their N-oxides and their physiologically acceptable addition salts with acids, processes for their preparation and pharmaceutical formulations which contain these compounds and are useful in the treatment of cardiac arrhythmias.

14 Claims, No Drawings

PYRIDINYL AMINOALKYL ETHERS

The present invention relates to new pyridinyl aminoalkyl ethers, their N-oxides and their physiologically acceptable addition salts with acids, processes for their preparation and pharmaceutical formulations which contain these compounds and are useful in the treatment of cardiac arrhythmias.

We have found that pyridinyl aminoalkyl ethers of the formula I

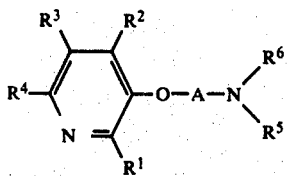

where $R^1$ is hydrogen, alkyl of 1 to 5 carbon atoms, alkenyl or alkynyl of 2 to 5 carbon atoms, hydroxymethyl, phenylalkyl of 7 to 9 carbon atoms or phenyl, the phenyl rings each being unsubstituted or mono-, di- or tri-substituted by hydroxyl, halogen, e.g. fluorine, chlorine, bromine or iodine, nitro, carboxyl, alkoxycarbonyl or alkoxy, alkyl in each case being of 1 to 3 carbon atoms, trifluoromethyl or alkyl of 1 to 5 carbon atoms, $R^2$ and $R^3$ are identical or different and each is hydrogen or alkyl of 1 to 3 carbon atoms, which is unsubstituted or substituted by hydroxyl, sulfhydryl, amino or alkoxy, alkylthio, alkylamino or dialkylamino, alkyl in each case being of 1 to 4 carbon atoms, or by acyloxy of 1 to 4 carbon atoms, or is formyl, carboxyl, alkoxycarbonyl, where alkyl is of 1 to 4 carbon atoms, amidocarbonyl or nitrile, or $R^2$ and $R^3$ together are $-CH_2-B-CH_2-$ and form, together with the carbon atoms by which they are linked, a 5-membered to 7-membered ring, B being alkylene $-(CH_2)_{1-3}-$, oxygen, sulfur, alkylidenedioxy

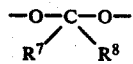

or imino

where $R^7$ and $R^8$ are hydrogen, alkyl of 1 to 5 carbon atoms or phenyl, and, $R^4$ is hydrogen, alkyl of 1 to 5 carbon atoms, phenylalkyl of 7 to 9 carbon atoms or phenyl, the phenyl rings each being unsubstituted or mono-, di- or tri-substituted by hydroxyl, halogen, e.g. fluorine, chlorine, bromine or iodine, nitro, carboxyl, alkoxycarbonyl or alkoxy, alkyl in each case being of 1 to 3 carbon atoms, trifluoromethyl or alkyl of 1 to 5 carbon atoms, or is α-thenyl and at least two of the radicals $R^1$ to $R^4$ are not hydrogen, and A is straight-chain or branched alkylene of 2 to 8 carbon atoms, which is saturated or unsaturated and unsubstituted or substituted by hydroxyl, $R^5$ is hydrogen, or alkyl of 1 to 6 carbon atoms which is unsubstituted or substituted by hydroxyl, alkoxy, alkylthio, alkylamino or dialkylamino, where alkyl is in each case of 1 to 4 carbon atoms, or by phenoxy or phenyl, the phenyl rings being unsubstituted or additionally substituted by alkyl or alkoxy of 1 to 3 carbon atoms, or is alkenyl or alkynyl of 3 to 6 carbon atoms, cycloalkyl, where the ring is of 3 to 8 carbon atoms and which is unsubstituted or substituted by alkyl of 1 to 3 carbon atoms, or phenyl, which is unsubstituted or substituted by alkyl or alkoxy, alkyl in each case being of 1 to 3 carbon atoms, with the carbon atoms by which they are linked, a 5-membered to 7-membered ring, B being alkylene $-(CH_2)_{1-3}-$, oxygen, sulfur, alkylidenedioxy

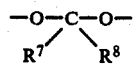

or imino

where $R^7$ and $R^8$ are hydrogen, alkyl of 1 to 5 carbon atoms or phenyl, and, $R^4$ is hydrogen, alkyl of 1 to 5 carbon atoms, phenylalkyl of 7 to 9 carbon atoms or phenyl, the phenyl rings each being unsubstituted or mono-, di- or tri-substituted by hydroxyl, halogen, eg. fluorine, chlorine, bromine or iodine, nitro, carboxyl, alkoxycarbonyl or alkoxy, alkyl in each case being of 1 to 3 carbon atoms, trifluoromethyl or alkyl of 1 to 5 carbon atoms, or is α-thenyl and at least two of the radicals $R^1$ to $R^4$ are not hydrogen, and A is straight-chain or branched alkylene of 2 to 8 carbon atoms, which is saturated or unsaturated and unsubstituted or substituted by hydroxyl, $R^5$ is hydrogen, or alkyl of 1 to 6 carbon atoms which is unsubstituted or substituted by hydroxyl, alkoxy, alkylthio, alkylamino or dialkylamino, where alkyl is in each case of 1 to 4 carbon atoms, or by phenoxy or phenyl, the phenyl rings being unsubstituted or additionally substituted by alkyl or alkoxy of 1 to 3 carbon atoms, or is alkenyl or alkynyl of 3 to 6 carbon atoms, cycloalkyl, where the ring is of 3 to 8 carbon atoms and which is unsubstituted or substituted by alkyl of 1 to 3 carbon atoms, or phenyl, which is unsubstituted or substituted by alkyl or alkoxy, alkyl in each case being of 1 to 3 carbon atoms, $R^6$ is hydrogen or alkyl of 1 to 6 carbon atoms, or $R^5$ and $R^6$ together with the N atom are a 4-membered to 8-membered ring which may or may not contain a further oxygen, nitrogen or sulfur atom and is unsubstituted or substituted by alkyl of 1 to 3 carbon atoms, cycloalkyl, where the ring is of 3 to 8 carbon atoms, hydroxyl, alkoxy of 1 to 4 carbon atoms or phenyl or phenylalkyl of 7 to 9 carbon atoms, the phenyl rings being unsubstituted or substituted by alkyl or alkoxy of 1 to 3 carbon atoms, their pyridine N-oxides and their physiologically acceptable addition salts with acids exhibit valuable pharmacological properties.

In accordance with the above meanings, if $R^1$ is alkyl of 1 to 5 carbon atoms it may be, for example, a straight-chain or branched radical, eg. methyl, ethyl, n-propyl, isopropyl, n-butyl, sec.-butyl, isobutyl, n-pentyl or isoamyl, whilst as alkenyl or alkynyl it may be, for example, vinyl or ethynyl, and as phenylalkyl it may be, for example, benzyl.

If $R^2$ and $R^3$ are alkyl of 1 to 3 carbon atoms they may be, for example, methyl, ethyl or isopropyl, if they are substituted alkyl they may be, for example, hydroxymethyl, methoxymethyl, ethoxymethyl, isobutoxymethyl, methylthiomethyl, dimethylaminomethyl or diethylaminomethyl and if they are alkoxycarbonyl, where alkyl is of 1 to 4 carbon atoms, they may be, for example, methoxycarbonyl, ethoxycarbonyl or n-butoxycarbonyl, whilst if they are —$CH_2$—B—$CH_2$ they may be, for example, trimethylene, 2-oxa-trimethylene, 2-thia-trimethylene or 2-aza-trimethylene, where examples of suitable substituents of the nitrogen are methyl, ethyl, isopropyl, isobutyl and phenyl.

If $R^4$ is alkyl of 1 to 5 carbon atoms it may be, for example, a straight-chain or branched radical, eg. methyl, ethyl, n-propyl, isopropyl, n-butyl, sec.-butyl, isobutyl, n-pentyl or isoamyl, whilst if it is substituted phenyl or phenylalkyl it may be, for example, p-methylphenyl, p-methoxyphenyl, benzyl, m-methylbenzyl, p-methylbenzyl, p-methoxybenzyl, 3,4-dimethoxybenzyl, m-hydroxybenzyl, p-ethoxybenzyl, m-chlorobenzyl, p-chlorobenzyl, p-bromobenzyl, p-fluorobenzyl, o-chlorobenzyl, p-iodobenzyl, α-phenylethyl, α-p-chlorophenylethyl, α-m-methylphenylethyl or β-phenylethyl.

Examples of aminoalkyl

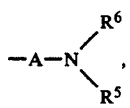

where A, $R^5$ and $R^6$ have the stated meanings, are 2-aminoethyl, 3-aminopropyl, 1-amino-2-propyl, 2-aminopropyl, 4-aminobutyl, 3-aminobutyl, 4-amino-2-butyl, 3-amino-2-methyl-propyl, 5-aminopentyl, 4-aminopentyl, 3-aminopentyl, 5-amino-2-pentyl, 4-amino-3-methyl-butyl, 5-amino-2-methyl-pentyl, 5-amino-3-methylpentyl, 4-amino-3-ethyl-butyl, 6-aminohexyl, 5-aminohexyl, 6-amino-2-hexyl, 4-aminohexyl or 6-aminooctyl, in which the amino groups may, as stated above, be unsubstituted, monosubstituted or disubstituted.

If $R^5$ is alkyl of 1 to 6 carbon atoms it may be, for example methyl, ethyl, n-propyl, isopropyl, n-butyl, sec.-butyl, isobutyl, tert.-butyl, 1,2-dimethylpropyl, n-pentyl or isoamyl, whilst as alkenyl or alkynyl of 3 to 6 carbon atoms it may be, for example, allyl, 3-buten-2-yl, propargyl pargyl, as substituted alkyl it may be, for example, 2-hydroxyethyl, 3-hydroxybutyl, 3-hydroxy-3-methylbutyl, 3-ethoxypropyl, 1-methoxy-2-propyl, 2-phenoxypropyl, 1-phenoxy-2-propyl, 3-dimethylaminopropyl, 3-ethylaminopropyl, 2-methylmercaptoethyl, benzyl, 2-phenylethyl, 2-o-methoxyphenylethyl, 2-p-methoxyphenylethyl or 3-phenylpropyl, and as cycloalkyl, where the ring is of 3 to 8 carbon atoms and which may or may not be substituted, it may be, for example, cyclopropyl, cyclobutyl, cyclopentyl, cyclohexyl, 2-methylcyclohexyl, cycloheptyl or cyclooctyl.

If $R^5$ has these meanings, $R^6$ is hydrogen or especially one of the unsubstituted alkyl radicals mentioned for $R^5$.

If $R^5$ and $R^6$ together with the nitrogen are a 4-membered to 8-membered ring, this may be, for example, pyrrolidine, 2-methylpyrrolidine, piperidine, 2-, 3- or 4-methylpiperidine, 4-phenylpiperidine, 4-phenyl-4-hydroxypiperidine, 4-p-methoxyphenylpiperidine, 4-benzylpiperidine, morpholine, 2,6-dimethylmorpholine, thiomorpholine, piperazine, 4-benzylpiperazine, 4-phenylpiperazine or 4-m-methoxyphenyl-piperazine.

Compounds of the formula I to be singled out are those where $R^1$ is hydrogen, alkyl of 1 to 5 carbon atoms or benzyl, $R^2$ and $R^3$ are identical or different and each is hydrogen, alkyl of 1 to 3 carbon atoms, methyl substituted by hydroxyl, alkoxy, alkylthio or dialkylamino, alkyl in each case being of 1 to 4 carbon atoms, formyl, carboxyl, alkoxycarbonyl, alkyl being of 1 to 4 carbon atoms, or nitrile, or $R^2$ and $R^3$ together are —$CH_2$—B—$CH_2$— and form a 5-membered ring with the carbon atoms by which they are linked, B being methylene, oxygen, sulfur or nitrogen, and the nitrogen being unsubstituted or substituted by alkyl of 1 to 5 carbon atoms or phenyl, $R^4$ is hydrogen, phenyl, benzyl or α- or β-phenylethyl, the phenyl rings being unsubstituted or substituted by hydroxyl, halogen, eg. fluorine, chlorine, bromine or iodine, or alkyl or alkoxy, alkyl being of 1 to 3 carbon atoms, and at least two of the radicals $R^1$ to $R^4$ are not hydrogen, and A is straight-chain or branched alkylene of 2 to 8 carbon atoms, which is saturated or unsaturated, or is 2-hydroxy-1,3-propylene and $R^5$ and $R^6$ have the above meanings, and their physiologically acceptable addition salts with acids.

Amongst the above, preferred compounds of the formula I are those where $R^1$ is hydrogen, alkyl of 1 to 4 carbon atoms or benzyl, $R^2$ and $R^3$ are alkoxycarbonyl, alkyl being of 1 to 3 carbon atoms, or $R^2$ and $R^3$ together are trimethylene, 2-oxatrimethylene or 2-methylaza-trimethylene and $R^4$ is benzyl, A is alkylene of 3 to 5 carbon atoms which is unsubstituted or methyl-substituted, or is 2-hydroxy-1,3-propylene, and $R^5$ is hydrogen or alkyl of 1 to 5 carbon atoms, which is unsubstituted or hydroxyl-substituted, or is benzyl, and $R^6$ is hydrogen or alkyl of 1 to 4 carbon atoms, or $R^5$ and $R^6$ together with the nitrogen are a pyrrolidine, piperidine or piperazine ring, and their physiologically acceptable addition salts with acids.

Accordingly, examples of compounds of the formula I which are to be singled out and are preferred are those where the pyridinyl radical is 4-benzyl-1,3-dihydrofuro[3,4-c]pyridin-7-yl, 4-benzyl-6-methyl-1,3-dihydrofuro[3,4-c]pyridin-7-yl, 4-benzyl-6-ethyl-1,3-dihydrofuro[3,4-c]pyridin-7-yl, 4-benzyl-6-isobutyl-1,3-dihydrofuro[3,4-c]pyridin-7-yl, 4,6-dibenzyl-1,3-dihydrofuro[3,4-c]pyridin-7-yl, 1-benzyl-3-methyl-6,7-dihydro-5-H-2-pyrindin-4-yl, 4-benzyl-2,6-dimethyl-2,3-dihydro-1-H-pyrrolo[3,4-c]pyridin-7-yl, 2-methyl-4,5-dicarbomethoxy-6-benzyl-pyridin-3-yl and 2-methyl-4,5-dicarboethoxy-6-benzylpyridin-3-yl.

Accordingly, examples of aminoalkyl radicals

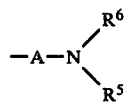

which are to be singled out and are preferred are 3-benzylaminopropyl, 3-di-n-propylaminopropyl, 4-tert.-butylamino-butyl, 5-isopropylamino-pentyl, 4-isopropylamino-but-2-enyl, 5-isopropylamino-3-methyl-pentyl, 5-diethylamino-3-methyl-pentyl, 3-N-piperazino-propyl, 4-diethylamino-butyl, 4-isopropylaminobutyl, 3-isopropylamino-propyl, 3-isopropylamino-2-hydroxypropyl, 3-diethylamino-2-hydroxy-propyl, 2-diethylamino-ethyl, 3-dimethylamino-propyl, 3-diethylamino-propyl, 3-piperidino-propyl, 3-pyrrolidino-propyl, 4-sec-butylaminobutyl, 4-tertbutylaminobutyl and 4-diisopropylaminobutyl.

The new compounds of the formula I can be prepared in accordance with the following processes.

1. A process for the preparation of pyridinyl aminoalkyl ethers of the general formula I and of their pyridine N-oxides, wherein a pyridinol of the general formula II

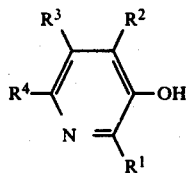

hereafter abbreviated P—OH, where $R^1$, $R^2$, $R^3$ and $R^4$ have the above meanings, or its N-oxide, is reacted with an alkylating agent of the general formula

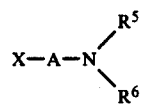

where X is a reactive esterified hydroxyl group and A, $R^5$ and $R^6$ have the above meanings, advantageously in a solvent and advantageously in the presence of a base, and, if desired, the resulting compound is converted to the addition salt with a physiologically acceptable acid.

Reactive, esterified hydroxyl groups X which deserve special mention are hydroxyl esterified with a strong inorganic or organic acid, especially a hydrohalic acid, eg. hydrochloric acid, hydrobromic acid or hydriodic acid, or sulfuric acid, or a strong organic sulfonic acid, eg. benzenesulfonic acid, methanesulfonic acid or 4-toluenesulfonic acid. Preferably, X is chlorine, bromine or iodine.

The reaction is advantageously carried out in the presence of an equivalent amount, or an excess, of a base, eg. an alkali metal hydroxide, carbonate or alcoholate of a lower monohydric alcohol, as the acid-binding agent, the sodium or potassium compounds being used in particular.

The reaction can also be carried out with the starting compound of the formula II in the form of its alkali metal salt, especially the sodium salt or potassium salt, which is directly obtainable from the compound P—OH of the formula II. To form the salt, the above alkali metal compounds are used or, especially if an aprotic solvent is employed, sodium or potassium amide or hydride may be used.

The reaction is advantageously carried out in a solvent at from 0° to 150° C., preferably from 20° to 100° C. Advantageous solvents are lower alcohols of 1 to 4 carbon atoms, especially methanol or ethanol, lower aliphatic ketones, especially acetone, benzene hydrocarbons, eg. benzene itself or alkylbenzenes or halobenzenes, eg. chlorobenzene or toluene, aliphatic or cyclic ethers, eg. diethyl ether, tetrahydrofuran or dioxane, dimethylformamide or dimethylsulfoxide. If an ether is used as the solvent, hexamethylphosphorotriamide may advantageously be added thereto as an auxiliary solvent.

In an advantageous variant, especially if no readily saponifiable functional groups are present in the pyridinol, two-phase solvent mixtures, especially mixtures of water with a chlorohydrocarbon, eg. methylene chloride, or a benzene hydrocarbon, eg. benzene or toluene, are used and the conventional method of phase transfer catalysis, as described, for example, by M. Makosza in Pure and Applied Chemistry, 1975, No. 43, 439, is employed. The preferred bases are in that case mixtures of an alkali metal hydroxide, especially sodium hydroxide, employed in at least molar amount, and a quaternary ammonium base or a phosphonium base employed, in catalytic amount, ie. from 1 to 10 mole % based on compound II, in the form of a salt, eg. triethylbenzylammonium chloride, tetrabutylammonium bisulfate or tributylhexadecylphosphonium bromide.

2. Process for the preparation of pyridinyl aminoalkyl ethers of the general formula I and their pyridine N-oxides, wherein a pyridinol of the general formula II, hereafter abbreviated P—OH, where $R^1$, $R^2$, $R^3$ and $R^4$ have the above meanings, or its pyridine N-oxide is reacted with a compound of the general formula X—A—Y, where X and Y are reactive esterified hydroxyl groups, especially chlorine, bromine or iodine, advantageously in a solvent and in the presence of a base as the acid-binding agent, and the resulting compound of the general formula III $$P—O—A—Y \qquad III$$

is then reacted with an amine of the formula $R^5$—N-H—$R^6$, where $R^5$ and $R^6$ have the above meanings, and, if desired, the end product is converted to an addition salt with a physiologically acceptable acid.

The process conditions for the preparation of the intermediate of the formula III correspond, in respect of the solvents employed, the bases used as acid-binding agents, and the temperatures, to the conditions described for process 1, and in particular the phase transfer method can also be used. In order to keep the formation of byproducts, especially etherification reactions with 2 moles of P—OH, at as low a level as possible, it is advantageous to use X—A—Y in at least a two-fold molar excess or as the solvent, or alternatively to use a compound in which, advantageously, X and Y are different, so that their different reactivity can be utilized, as is the case, for example, with the different reactivities of bromine and chlorine.

The intermediate of the formula III can be isolated and then be reacted as such with an amine $R^5$—N-H—$R^6$, or can be reacted directly, in the reaction mixture obtained from the first process step, with the amine, in which case it is advantageous first to remove unconverted alkylating agent.

This reaction, like that described for process 1, is advantageously carried out in a solvent and in the presence of a base. An excess of the amine $R^5$—NH—$R^6$ can also be used as the base and can also at the same time serve as the solvent. The reaction is carried out at an elevated temperature, in general at from 60° to 120° C., under atmospheric pressure or, where appropriate, in a closed vessel under superatmospheric pressure, especially if a very volatile amine is used.

3. Pyridinyl aminoalkyl ethers of the general formula I and their pyridine N-oxides can also be prepared by a process wherein an amine of the general formula IV or its pyridine N-oxide

P—O—A—NH$_2$    IV is reacted with an alkylating agent R$^5$-X and/or R$^6$-X, where R$^5$ and R$^6$ have the above meanings, and X has the meanings given in connection with process 1, in the conventional manner, or wherein a compound of the general formula IV is reacted with an aliphatic ketone corresponding to the meanings of R$^5$ and R$^6$ under reductive amine-alkylation conditions.

The direct amine-alkylation is advantageously carried out in a lower alcohol, preferably methanol or ethanol, and in the presence of a base, preferably sodium carbonate, as the acid-binding agent, at room temperature or at elevated temperatures, up to the reflux temperature.

To prepare a compound of the general formula I, where R$^5$ is secondary alkyl and R$^6$ is hydrogen, under the reductive amine-alkylation conditions, the reaction is preferably carried out as a catalytic hydrogenation in the presence of platinum.

The compounds of the general formula IV can be prepared by heating compounds of the general formula III, dissolved in a lower alcohol, eg. ethanol, with excess ammonia in a closed system. They can also be prepared by heating compounds of the general formula III, dissolved in a polar solvent, especially dimethylformamide, with potassium phthalimide, to form the corresponding phthalimide derivatives of the general formula

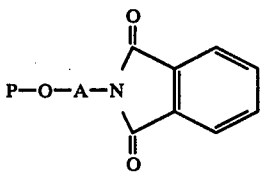

which are then reacted with hydroxylamine, preferably in a lower alcohol, eg. methanol, and in the presence of an alcoholate, eg. sodium methanolate.

4. Pyridinyl 3-amino-2-hydroxy-propyl ethers of the general formula V, where P—O— has the meanings given in connection with formula II and A is 2-hydroxytrimethylene

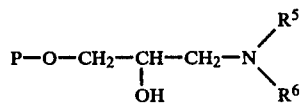

and their pyridine N-oxides can advantageously be prepared by a process wherein a glycidyl ether of the general formula VI

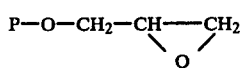

where P—O— has the meanings given in connection with formula II, is reacted with an amine R$^5$—NH—R$^6$, advantageously in a solvent, at from 0° to 120° C., in the conventional manner, and the resulting compound is then converted, if desired, to the corresponding pyridine N-oxide and/or to an addition salt with a physiologically acceptable acid.

The glycidyl ethers of the general formula VI are obtainable, for example, from a pyridinol of the formula II and epichlorohydrin in the conventional manner. The reaction is preferably carried out in the presence of a base, such as an alkali metal carbonate, and in a polar solvent. It is also possible, as described above, to use an alkali metal salt of a pyridinol of the formula II, which can be obtained from the pyridinol II by reaction with an alkali metal carbonate, alkali metal alcoholate, alkali metal amide or alkali metal hydride, e.g. sodium amide or sodium hydride.

The resulting glycidyl ether of the formula VI can be isolated as such and then be reacted with an amine R$^5$—NH—R$^6$, or can also be treated with the amine directly in the reaction mixture. The reaction is advantageously carried out in a solvent, especially acetone, acetonitrile, dimethylformamide or dimethylsulfoxide. Excess amine can also serve as the solvent. The reaction is preferably carried out at from room temperature to 100° C., under atmospheric pressure or in a closed vessel under superatmospheric pressure, especially if a readily volatile amine is used.

The new compounds of the formula I can also be obtained by a process wherein, in a compound of the formula I which contains a removable radical on the nitrogen of the amino group and/or on the hydroxyl group of the alkylene chain A, this radical or these radicals are split off by solvolysis or reduction reactions.

Radicals which can be split off by solvolysis are especially those removable by hydrolysis or ammonolysis. Examples of radicals which can be split off by hydrolysis are acyl, sulfonyl or cyano. Compounds with radicals which can be split off by hydrolysis for example also include compounds of the formula VII

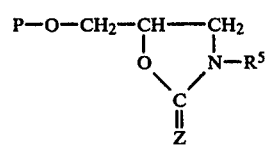

where Z is oxygen or sulfur and R$^5$ has the above meanings. The hydrolysis is carried out in the conventional manner, for example in the presence of acids or bases, eg. aqueous mineral acids, especially sulfuric acid or a hydrohalic acid, or in the presence of basic agents, especially alkali metal hydroxides, eg. sodium hydroxide.

Further, it is possible, for example, to split off a tert.-butoxycarbonyl radical under anhydrous conditions in the conventional manner by treatment with a suitable acid, eg. trifluoroacetic acid.

Radicals which can be split off reductively are, for example, α-arylalkyl radicals, eg. benzyl, or α-aralkoxycarbonyl radicals, eg. benzyloxycarbonyl, which can be split off in the conventional manner by hydrogenolysis, especially by catalytically activated hydrogen, eg. hydrogen in the presence of a hydrogenation catalyst, eg. Raney nickel. A radical which can be split off reductively may also be an arylsulfonyl group, eg. toluenesulfonyl. Of course, care must be taken that during hydrogenolysis other reducible groups are not attacked.

Depending on the process conditions and the starting compounds, the compounds according to the invention are obtained in the free form or in the form of their acid addition salts which are also encompassed by the invention. These salts may be basic, neutral or mixed salts and may or may not be in the form of hydrates. the acid addition salts obtained during the process of preparation may be converted to the free base in the conventional manner by means of basic agents, eg. alkali or ion exchangers. On the other hand, the free bases obtained can also be directly converted to the salts with organic or inorganic acids. The pyridine N-oxides can also be obtained in the conventional manner, in cases where a pyridine N-oxide of the formula II has not been used as the starting compound.

The acids used for the preparation of the addition salts are especially those which are capable of forming therapeutically acceptable salts. Examples of these are hydrohalic acids, sulfuric acid, phosphoric acid, nitric acid, fumaric acid and aliphatic, alicyclic, aromatic or heterocyclic carboxylic acids or sulfonic acids, e.g. formic acid, acetic acid, propionic acid, succinic acid, glycollic acid, lactic acid, malic acid, tartaric acid, citric acid, ascorbic acid, maleic acid, pyruvic acid, benzoic acid, anthranilic acid, p-hydroxybenzoic acid, salicylic acid, methanesulfonic acid, ethanesulfonic acid, hydroxyethanesulfonic acid, ethylenesulfonic acid, halobenzenesulfonic acids, toluene-sulfonic acid, cyclohexylaminesulfonic acid and sulfanilic acid, and further examples may be found in Fortschritte der Arzneimittelforschung, volume 10, pages 224–225, Birkhäuser Verlag, Basel and Stuttgart, 1966.

At times, the conversion to an addition salt with an acid may in particular be used to purify the compound obtained, by converting the free base to a salt, isolating the latter, recrystallizing it if required, and again liberating the base from this salt. Picrates, perchlorates and hydrohalides, especially hydrobromides and hydrochlorides, are examples of suitable salts for this purpose.

Depending on the selection of the starting compounds and the methods used, the new compounds may be in the form of optical antipodes or racemates, or of diastereomer mixtures. The diastereomer mixtures obtained can be separated into the diastereomers in the conventional manner, for example by chromatography and/or fractional crystallization. Racemates obtained can be resolved into the optical antipodes by conventional methods, for example by reaction with an optically active acid which forms salts with the racemic compound, and separation into the diastereomers, or by means of microorganisms, or by recrystallization from an optionally active solvent. Examples of optically active acids which are used particularly extensively are the D- and L-forms of tartaric acid, malic acid, mandelic acid and camphorsulfonic acid.

The starting compounds of the formula II can be prepared, for example, by reacting an oxazole of the formula VIII

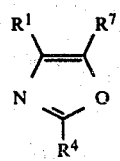

VIII where $R^1$ and $R^4$ have the meanings given for the formula II and $R^7$ is hydrogen, alkoxy of 1 to 5 carbon atoms or nitrile, with an olefin of the formula IX

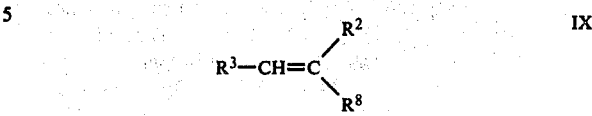

IX where $R^2$ and $R^3$ have the meanings given for formula I and $R^8$ is hydrogen, alkylsulfonyl of 1 to 5 carbon atoms or phenylsulfonyl, but at least one of $R^7$ and $R^8$ is hydrogen, at from 20° to 200° C., the reaction being carried out in the presence of a dehydrogenating agent if both $R^7$ and $R^8$ are hydrogen; the compound obtained may or may not be converted to the pyridine N-oxide, or to an addition salt with an acid, by conventional methods.

The above reaction of an oxazole VIII with an olefin IX corresponds to the conventional Diels-Alder reaction and is disclosed in the literature, for example Russ. Chem. Rev. 38 (1969), 540–546 or Chemiker-Zeitung 100 (1976), 105–111.

The preferred temperature range of this reaction is from 50° to 180° C. and the starting compounds are used in a molar ratio of from 1:5 to 5:1. Advantageously, the reaction is carried out in the absence of a solvent and in certain cases the excess component can serve as a solvent. Where a solvent is added, suitable materials are substituted and unsubstituted aromatic and aliphatic hydrocarbons, eg. nitrobenzene, chlorobenzene, dichlorobenzene, toluene and xylene, aliphatic and cyclic ethers and lower alcohols, eg. diethyl ether, tetrahydrofuran, 1,2-diethoxyethane, ethanol and methanol, as well as dimethylformamide and dimethylsulfoxide.

The end of the reaction can easily be detected, for example by thin layer chromatography, and the reaction product is worked up in the conventional manner.

Preferred starting compounds of the formulae VIII and IX are those where $R^7$ is methoxy, ethoxy, propoxy, isobutoxy or nitrile and $R^8$ is hydrogen, or those where $R^7$ is hydrogen and $R^8$ is methylsulfonyl, ethylsufonyl, n-butylsulfonyl or phenylsulfonyl, the remaining substituents having the above meanings.

Where both $R^7$ and $R^8$ are hydrogen, the reaction is carried out in the presence of a dehydrogenating agent. Nitrobenzene has proved particularly suitable for this purpose.

The compounds obtained may or may not be converted to their pyridine N-oxides in the conventional manner, as disclosed, for example, in Angew. Chemie 70 (1958), 731 et seq.

The oxidizing agent used is hydrogen peroxide, especially in the form of a solution of from 10 to 50% strength by weight in water or acetic acid, or in the form of its inorganic or organic derivatives.

Examples of organic derivatives of hydrogen peroxide are per-acids, eg. peracetic acid, peroxytrifluoroacetic acid, perbenzoic acid, m-chloroperbenzoic acid and monoperphthalic acid, and alkyl hydroperoxides, eg. tert.-butyl hydroperoxide, whilst an example of an inorganic derivative is peroxydisulfuric acid.

The N-oxidation is advantageously carried out in a solvent, eg. water or chloroform, or, when using per-acids, especially in the acids on which these are based, or in mixtures of the said solvents.

In some cases it is advantageous to provide the phenolic hydroxyl group, by esterification, with an easily removable protective group, advantageously with an acetyl group, before carrying out the N-oxidation.

The oxazoles VIII used as starting compounds are known compounds or can be prepared, without difficulties, by processes described in the literature, for example in Chem. Rev. 75 (1975), 389–402, Adv. Heter. Chem. 17 (1974), 99–149, German Laid-Open Application DOS 2,152,367 and German Laid-Open Application DOS 2,451,725.

Similar remarks apply to the olefins of the formula IX, which may be prepared, for example, as described in Synthesis 1971, pages 563–573, J. Chem. Soc. 1964, 4,962–4,971, J. Org. Chem. 35 (1970) 4,220–4,221, German Laid-Open Application DOS 2,143,989 or German Laid-Open Application DOS 2,435,098.

We draw attention to the fact that pyridinols of the formula II and their preparation form the subject of the copending German Patent Application P No. 27 11 656.9 (O.Z. 32,486) of the same date.

The compounds according to the invention exhibit valuable pharmacological properties. They are distinguished by a powerful anti-arrhythmic and/or local-anaesthetic action. They are particularly suitable for use in the pharmacotherapy of cardiac arrhythmias.

Accordingly, the present invention also relates to therapeutic agents or formulations which, in addition to conventional excipients and diluents, contain, as the active ingredient, a compound of the formula I, its N-oxide or one of its physiologically acceptable addition salts with an acid, and to the use of the new compounds, especially in cases of cardiac arrhythmias.

To determine the anti-arrhythmic activity, the drugs were administered orally to rats (Sprague Dawley, weight from 180 to 240 g) 45 minutes before the start of the narcosis.

The animals were narcotized with thiobutabartial (100 mg/kg administered intraperitoneally). The arrhythmogenic substance used was aconitine, which was administered by intravenous infusion (at a rate of 0.005 mg/kg.min) 60 minutes after administration of the test substance. In the case of untreated animals (N=30), arrhythmias occurred after an average of 3.7±0.9 minutes, the commencement of which can be delayed by anti-arrhythmic agents, the delay depending on the dosage.

For a quantitative evaluation of the linear relation between log dose (mg/kg) of the test substances and relative prolongation of the duration of aconitine infusion ($\Delta\%$), the dose which extended the duration of infusion by 50% (ED 50) was determined. The prior art anti-arrhythmic agent quinidine served as a comparative substance.

The acute toxicity was determined on groups of 10 or 20 female Swiss mice, weighing 20–26 g, the compounds being administered intraperitoneally. The LD 50 was calculated as the dose (Probit analysis) after which 50% of the animals died within 24 hours.

As is apparent from Table 1, the compounds according to the invention are distinguished by an anti-arrhythmic action which is up to 7.5 times more powerful than that of quinidine (Table 1, Example 47). A further advantage is that the effect achieved with the maximum dose is from 1.2 (Example 43) to 3.4 (Example 34) times as great as that of quinidine, ie. the aconitine-antagonism of the tested compounds is substantially more pronounced than that of quinidine.

The therapeutic range, expressed as the quotient of the 50% lethal dose (LD 50) and the 50% anti-arrhythmically effective dose (ED 50) ranges from being as great as (Example 68) to 4.1 times as great as (Example 47) that of quinidine.

TABLE 1

| | Anti-arrhythmic action and acute toxicity | | | | | | |
|---|---|---|---|---|---|---|---|
| | Anti-arrhythmic action (1) | | | | | Acute toxicity | Therapeutic range |
| Example No. | Effective dose | | Maximum action (4) | | | | |
| | ED 50 (2) | R.A. (3) | Dose | $\Delta\%$ (5) | R.M.A. (6) | LD 50 | (7) |
| Quinidine | 42.3 | 1.00 | 215 | 133 | 1.00 | 180 | 4.26 |
| 1 | 31.0 | 1.36 | 68.1 | 184 | 1.38 | about 147 | about 4.74 |
| 18 | 9.82 | 4.35 | 215 | 295 | 2.22 | 170 | 17.31 |
| 25 | 15.9 | 2.67 | 100 | 195 | 1.47 | 137 | 8.62 |
| 29 | 18.1 | 2.34 | 215 | 271 | 2.04 | 104 | 5.75 |
| 32 | 14.9 | 2.84 | 215 | 319 | 2.40 | 98.3 | 6.60 |
| 34 | 28.9 | 1.46 | 215 | 457 | 3.44 | 139 | 4.81 |
| 36 | 21.0 | 2.01 | 100 | 219 | 1.65 | 180 | 8.57 |
| 43 | 28.5 | 1.48 | 46.4 | 154 | 1.16 | about 147 | about 5.16 |
| 47 | 5.66 | 7.47 | 100 | 358 | 2.69 | 99.3 | 17.54 |
| 52 | 16.0 | 2.64 | 215 | 225 | 1.69 | 104 | 6.50 |
| 55 | 12.2 | 3.47 | 100 | 333 | 2.50 | 82.2 | 6.74 |
| 57 | 11.3 | 3.74 | 100 | 261 | 1.96 | 88.9 | 7.86 |
| 58 | 18.8 | 2.27 | 100 | 186 | 1.40 | 114 | 6.06 |
| 60 | 21.1 | 2.00 | 100 | 246 | 1.85 | 101 | 4.79 |
| 61 | 9.29 | 4.60 | 46.4 | 298 | 2.24 | 73.9 | 7.95 |
| 64 | 21.2 | 2.01 | 100 | 317 | 2.38 | 156 | 7.36 |
| 69 | 23.0 | 1.84 | 464 | 218 | 1.64 | 107 | 4.65 |
| 68 | 15.8 | 2.70 | 100 | 241 | 1.81 | about 68.1 | about 4.31 |

Notes on Table 1:
(1) Aconitine-induced arrhythmia, rats
(2) Dose (mg/kg), administered orally, which extends the duration of aconitine infusion (in minutes) by 50%
(3) R.A. = relative activity; quinidine = 1.00
(4) Action of the highest non-toxic dose
(5) Prolongation of the duration of aconitine infusion, $\Delta\%$
(6) R.M.A. = relative maximum activity
(7) $\dfrac{\text{LD 50}}{\text{ED 50}}$ With respect to the effects referred to, the Table shows that very particularly preferred compounds are those of the formula I where $R^1$ is methyl, ethyl or benzyl, $R^2$ and $R^3$ are alkoxycarbonyl, alkyl being of 1 to 3 carbon atoms, or $R^2$ and $R^3$ together are 2-oxatrimethylene and $R^4$ is benzyl, and A is a polymethylene chain of 3 to 5 carbon atoms which is unsubstituted or substituted by methyl, or is 2-hydroxy-1,3-propylene, $R^5$ is hydrogen or alkyl of 1 to 4 carbon atoms and $R^6$ is alkyl of 1 to 4 carbon atoms, and their physiologically acceptable addition salts with acids.

The therapeutic agents or formulations are prepared in the conventional manner by compounding an appropriate dose with the conventional excipients or diluents and the conventional pharmaceutical auxiliaries, in accordance with the desired route of administration.

The preferred formulations are those suitable for oral administration. Examples of these are tablets, film tablets, dragées, capsules, pills, powders, solutions or suspensions, or forms which exert a depot effect.

Of course, formulations for parenteral administration, eg. injection solutions, or additives for infusion solutions, are also suitable. Suppositories are a further example of suitable formulations.

Appropriate tablets can be obtained, for example, by mixing the active ingredient with conventional auxiliaries, for example inert excipients, eg. dextrose, sugar, sorbitol, mannitol, polyvinylpyrrolidone, calcium carbonate, calcium phosphate or lactose, disintegrating agents, eg. corn starch, alginic acid or polyvinylpyrrolidone, binders, eg. starch or gelatin, lubricants, eg. magnesium stearate or talc, and/or agents added in order to achieve a depot effect, eg. carboxypolymethylene, carboxymethylcellulose, cellulose acetate phthalate or polyvinyl acetate. The tablets may also consist of a plurality of layers.

Dragées may be produced correspondingly by coating cores, prepared similarly to the tablets, with agents conventionally used in dragée coatings, for example polyvinylpyrrolidone or shellac, gum arabic, talc, titanium dioxide or sugar. The dragée coating may also consist of a plurality of layers, and the auxiliaries referred to above in connection with tablets may be employed.

Solutions or suspensions containing the active ingredients according to the invention may in addition contain agents for improving the taste, eg. saccharin, cyclamate or sugar, as well as, for example, flavorings, eg. vanillin or orange extract. Furthermore, they may contain dispersants, eg. sodium carboxymethylcellulose, or preservatives, eg. parahydroxybenzoates. Capsules containing the active ingredient may be produced, for example, by mixing the active ingredient with an inert excipient, eg. lactose or sorbitol, and encapsulating the mixture in gelatin capsules.

Suitable suppositories may be produced, for example, by mixing the active ingredient with an appropriate excipient, eg. a neutral fat or polyethylene glycol or a derivative thereof.

For man, a single dose of a compound according to the invention is from 5 to 100 mg, preferably from 10 to 80 mg.

The Examples which follow illustrate the invention without implying any limitation. Preparation of the starting compounds of the formula II

EXAMPLE I

4-Benzyl-6-methyl-1,3-dihydro-furo[3,4-c]pyridin-7-ol

A mixture of 296 g (2 moles) of 3-methylsulfonyl-2,5-dihydrofuran and 692 g (4 moles) of 2-benzyl-4-methyloxazole is heated for 20 hours at 150° C. When it has cooled, the mixture is suspended in 1 l of methylene chloride. The solution contains unconverted oxazole. The undissolved constituent is a mixture of 4-benzyl-6-methyl-1,3-dihydrofuro[3,4-c]pyridin-7-ol and 3,4-dimethylsulfonyl-tetrahydrofuran, which is separated by digesting in 1.35 l of nitromethane. 186 g of 4-benzyl-6-methyl-1,3-dihydro-furo[3,4-c]pyridin-7-ol, of melting point 212°–214° C., remain undissolved. After recrystallization from methanol, the melting point is 215° C.

C, H and N determination ($C_{15}H_{15}NO_2$; 241)

Found: C 74.4%; H 6.2%; N 6.2% Calculated: 74.7 6.2 5.8

The hydrochloride, when recrystallized from water, melts at 251° C.

The reaction can also be carried out with 3-ethylsulfonyl-2,5-dihydrofuran or 3-phenylsulfonyl-2,5-dihydrofuran.

EXAMPLE II

4-Benzyl-6-ethyl-1,3-dihydro-furo[3,4-c]pyridin-7-ol (a) 2-Benzyl-4-ethyloxazole 128 g (0.5 mole) of phenylacetimido-cyclohexyl ester hydrochloride are introduced, at room temperature, into a mixture of 23 g (0.25 mole) of 2-ketobutanol and 100 g of N,N-dimethylaniline. The mixture is heated for 2.5 hours at 100° C., 250 ml of 10% strength sodium hydroxide solution are added after cooling, and the batch is extracted with methylene chloride. After distilling off the solvent, the residue is subjected to fractional distillation. 9.5 g of 2-benzyl-4-ethyloxazole, boiling point 74°–76° C./0.2 mm Hg, are obtained.

(b) 9.4 g (50 millimoles) of 2-benzyl-4-ethyloxazole and 29.6 g (200 millimoles) of 3-methylsulfonyl-2,5-dihydrofuran are heated for 15 hours at 150° C. Unconverted sulfone is distilled off in a high vacuum. The residue is digested in methylene chloride, the undissolved constituent is filtered off and the filtrate is extracted with 150 ml of 10% strength sodium hydroxide solution. The alkaline solution is neutralized and extracted with methylene chloride. On concentrating the methylene chloride solution, 6.2 g of 4-benzyl-6-ethyl-1,3-dihydro-furo[3,4-c]pyridin-7-ol remain. Melting point after recrystallization from nitromethane: 148° C.

C, H and N determination ($C_{16}H_{17}NO_2$; 255)

Found: C 75.2%; H 6.7%; N 5.6% Calculated 75.3 6.7 5.5

EXAMPLE III 4,6-Dibenzyl-1,3-dihydro-furo[3,4-c]pyridin-7-ol 44 g (150 millimoles) of 2,4-dibenzyl-5-ethoxyoxazole and 210 g (3 moles) of 2,5-dihydrofuran are heated for 8 hours at 180° C. Excess 2,5-dihydrofuran is distilled off and the residue is digested in ether. The undissolved constituent is recrystallized from ethanol. 17.6 g of 4,6-dibenzyl-1,3-dihydro-furo[3,4-c]pyridin-7-ol are obtained; melting point 204°–205° C.

C, H and N determination ($C_{21}H_{19}NO_2$; 317)

Found: C 79.4%; H 6.2%; N 4.5% Caclulated: 79.5 6.0 4.4

Preparation of compounds according to the invention

EXAMPLE 1

(a) 12.1 g (50 millimoles) of 4-benzyl-6-methyl-1,3-dihydro-furo[3,2-c]pyridin-7-ol are suspended in 40 ml of dry dimethylsulfoxide and converted to the sodium salt by adding 1.75 g (60 millimoles) of sodium hydride (85% strength in oil) at 20° C. When the evolution of hydrogen has ceased, 8.1 g (75 millimoles) of freshly distilled β-dimethylaminoethyl chloride are added dropwise and the mixture is left to stand for 15 hours at 10° C. The dimethylsulfoxide is distilled off in a high vacuum. The residue is taken up in methylene chloride, the salts and unconverted pyridinol are washed out with dilute sodium hydroxide solution, and the organic phase is dried and concentrated under reduced pressure. The residue is converted to the hydrochloride by means of dilute hydrochloric acid, and the hydrochloride is recrystallized from ethanol/ether. 10.0 g of 4-benzyl-6-methyl-1,3-dihydro-furo[3,4-c]pyridin-7-yl β-dimethylaminoethyl ether bis-hydrochloride are obtained; melting point 213°–214° C.

(b) 12.1 g (50 millimoles) of 4-benzyl-6-methyl-1,3-dihydro-furo[3,4-c]pyridin-7-ol are dissolved in 25 ml of 2-normal aqueous sodium hydroxide solution. After evaporating off the water, finally under reduced pressure at 100° C., the residue is suspended in 50 ml of tetrahydrofuran to which 5 ml of hexamethylphosphorotriamide have been added. 8.1 g (75 millimoles) of freshly distilled β-dimethylaminoethyl chloride are added dropwise and the mixture is boiled for 10 hours. After distilling off the tetrahydrofuran, the mixture is worked up as described under (a). 9.3 g of 4-benzyl-6-methyl-1,3-dihydro-furo[3,4-c]pyridin-7-yl β-dimethylaminoethyl ether bis-hydrochloride are obtained; melting point 213°–214° C.

The compounds shown in Table 2 which follows are prepared by the method described in Example 1 (c), and obtained in comparably high yield:

TABLE 2

| Ex. | $R^1$ | $R^2$ | $R^3$ | $R^4$ | Melting point °C. | %N Calc. | %N Found |
|---|---|---|---|---|---|---|---|
| 1 | $CH_3$ | $CH_2OCH_2$ | | $C_6H_5CH_2$ | 213–214 | 7.3 | 7.3 |
| 2 | $CH_3$ | $CH_2OCH_2$ | | $C_6H_5$ | 161–163 | 7.5 | 7.5 |
| 3 | $CH_3$ | $CH_2CH_2CH_2$ | | $C_6H_5CH_2$ | 198 | 7.3 | 6.9 |

EXAMPLE 4

12.1 g (50 millimoles) of 4-benzyl-6-methyl-1,3-dihydro-duro[3,4-c]pyridin-7-ol are converted to the sodium salt as described in Example 1 (a) and reacted with 10.2 g (75 millimoles) of β-diethylaminoethyl chloride. Working up as described in Example 1 (a) gives 12.6 g of 4-benzyl-6-methyl-1,3-dihydro-furo[3,4-c]pyridin-7-yl β-diethylaminoethyl ether bis-hydrochloride, which is recrystallized from acetonitrile; melting point 188° C.

The compounds shown in Table 3 are prepared in the same manner:

TABLE 3

| Example | $NR^5R^6$ | Melting point, °C. | %N Calc. | %N Found |
|---|---|---|---|---|
| 4 | $N(C_2H_5)_2$ | 188 | 6.8 | 6.8 |
| 5 | $N(CH(CH_3)_2)_2$ | 168–170 | 6.3 | 6.3 |
| 6 | pyrrolidinyl | 215 | 6.9 | 6.8 |
| 7 | piperidinyl | 225–227 | 6.6 | 6.6 |
| 8 | morpholinyl | 228–230 | 6.6 | 6.7 |

EXAMPLES 9 AND 10

12.1 g (50 millimoles) of 4-benzyl-6-methyl-1,3-dihydro-furo[3,4-c]pyridin-7-ol are converted to the sodium salt as described in Example 1 (a) and reacted with 9.2 g (75 millimoles) of N-(2-chloropropyl)-N,N-dimethylamine. Working up as described in Example 1 (a) gives a mixture of the two isomeric ethers shown below, which is separated by chromatography on silica gel (ethyl acetate/methanol).

4-Benzyl-6-methyl-1,3-dihydro-furo[3,4-c]pyridin-7-yl 1-diethylamino-2-propyl ether bis-hydrochloride, melting point 136°–138° C. (after recrystallization from ethanol/ether).

Calculated 7.0% N; found 6.7% N

4-Benzyl-6-methyl-1,3-dihydro-furo[3,4-c]pyridin-7-yl 2-diethylamino-1-propyl ether bis-hydrochloride, melting point 220° C. (after recrystallization from ethanol/ether). Calculated 7.0% N; found 6.8% N

EXAMPLE 11

12.1 g (50 millimoles) of 4-benzyl-6-methyl-1,3-dihydro-furo[3,4-c]pyridin-7-ol are converted to the sodium salt as described in Example 1 (a) and reacted with 9.2 g (75 millimoles) of N-(3-chloropropyl)-N,N-dimethylamine. Working up as described in Example 1 (a) gives 16.0 g of 4-benzyl-6-methyl-1,3-dihydro-furo[3,4-c]pyridin-7-yl 3-dimethylaminopropyl ether bis-hydrochloride, which is recrystallized from isopropanol/ethanol; melting point 202°–204° C.

The compounds listed in Table 4 are prepared by the method of Example 11.

TABLE 4

Structure: pyridine ring with $R^2$, $R^3$, $R^4$ substituents and $-O-(CH_2)_3-N(CH_3)_2 \cdot 2HCl$ group, with $R^1$ at position adjacent to N.

| Example | $R^1$ | $R^2$ | $R^3$ | $R^4$ | Melting point, °C. | %N Calc. | %N Found |
|---|---|---|---|---|---|---|---|
| 11 | $CH_3$ | | $CH_2OCH_2$ | $C_6H_5CH_2$ | 202–204 | 7.0 | 7.1 |
| 12[d] | $CH_3$ | | $CH_2OCH_2$ | $C_6H_5CH_2$ | 169 | 6.7 | 6.6 |
| 13 | $CH_3$ | | $CH_2OCH_2$ | $C_6H_5CH_2CH_2$ | 200 | 6.8 | 6.7 |
| 14[a] | $CH_3$ | | $CH_2OCH_2$ | 3-$CH_3$—$C_6H_4CH_2$ | 153–155 | 7.4 | 7.4 |
| 15[a] | $CH_3$ | | $CH_2OCH_2$ | 3-Cl—$C_6H_4CH_2$ | 123–125 | 7.1 | 7.0 |
| 16[a] | $CH_3$ | | $CH_2OCH_2$ | 4-Cl—$C_6H_4CH_2$ | 126–127 | 7.1 | 6.9 |
| 17 | $CH_3$ | | $CH_2OCH_2$ | $C_6H_5CH(CH_3)$ | 184–185 | 6.8 | 6.6 |
| 18 | $CH_3$ | $CO_2CH_3$ | $CO_2CH_3$ | $C_6H_5CH_2$ | 159–160 | 5.9 | 6.0 |
| 19 | $CH_3$ | $CO_2C_2H_5$ | H | $C_6H_5CH_2$ | 178–179 | 6.5 | 6.6 |
| 20 | $CH_3$ | | $CH_2OCHOCH_2$ $\mid$ $CH(CH_3)_2$ | $C_6H_5CH_2$ | 192–193 | 5.9 | 6.0 |
| 21[b] | $CH_3$ | | $CH_2N(CH_3)CH_2$ | $C_6H_5CH_2$ | 198 | 9.4 | 9.3 |
| 22[b] | $CH_3$ | $CH_2OH$ | $CH_2OH$ | $C_6H_5CH_2$ | 115 | 7.4 | 7.2 |
| 23 | $CH_3$ | $CH_2OCH_3$ | $CH_2OCH_3$ | $C_6H_5CH_2$ | 138 | 6.3 | 6.1 |
| 24[d] | $CH_3$ | $CH_2N(CH_3)_2$ | H | $C_6H_5CH_2$ | 153–155 | 9.8 | 9.6 |
| 25 | $CH_3$ | $CO_2C_2H_5$ | $CO_2C_2H_5$ | $C_6H_5CH_2$ | 150–152 | 5.6 | 5.6 |
| 26 | $CH_3$ | H | $CH_2OCH_3$ | $C_6H_5CH_2$ | 196 | 7.0 | 6.9 |
| 27 | $CH_3$ | $CH_2OCH_3$ | H | $C_6H_5CH_2$ | 181–183 | 7.0 | 6.9 |
| 28 | H | | $CH_2OCH_2$ | $C_6H_5CH_2$ | 189–190 | 7.3 | 7.2 |
| 29 | $C_2H_5$ | | $CH_2OCH_2$ | $C_6H_5CH_2$ | 106–108 | 6.8 | 6.5 |
| 30[c] | $CH(CH_3)_2$ | | $CH_2OCH_2$ | $C_6H_5CH_2$ | glassy | 5.4 | 5.2 |
| 31[a] | $CH_2CH(CH_3)_2$ | | $CH_2OCH_2$ | $C_6H_5CH_2$ | glassy | 6.9 | 6.7 |
| 32 | $C_6H_5CH_2$ | | $CH_2OCH_2$ | $C_6H_5CH_2$ | 115 | 5.9 | 5.6 |
| 33 | $C_6H_5CH_2$ | | $CH_2OCH_2$ | H | 192–193 | 7.3 | 7.0 |

[a]Mono-hydrochloride
[b]Tris-hydrochloride
[c]Bis-hydrobromide
[d]As the N-oxide

EXAMPLE 34

(a) A mixture of 24.2 g (100 millimoles) of 4-benzyl-6-methyl-1,3-dihydro-furo[3,4-c]pyridin-7-ol, 113 g (1 mole) of 1,3-dichloropropane, 2 g of benzyltriethylammonium chloride, 100 ml of toluene and 100 g of 50% strength sodium hydroxide solution is heated at 90° C. for 3 hours, whilst stirring. The organic phase is separated off and washed with 50 ml of water. After stripping off the solvent and the excess 1,3-dichloropropane, 30.7 g of 4-benzyl-6-methyl-1,3-dihydro-furo[3,4-c]pyridin-7-yl 3-chloropropyl ether, containing a small proportion of 1,3-bis-(4-benzyl-6-methyl-1,3-dihydro-furo[3,4-c]pyridin-7-oxy)-propane, which does not interfere with the subsequent reaction, remain.

(b) A mixture of 24.2 g (100 millimoles) of 4-benzyl-6-methyl-1,3-dihydro-furo[3,4-c]pyridin-7-ol, 226 g (2 moles) of 1,3-dichloropropane, 2 g of benzyltriethylammonium chloride and 100 g of 50% strength sodium hydroxide solution is heated at 90° C. for 3 hours, whilst stirring. The organic phase is separated off and washed with 50 ml of water. After stripping off the excess 1,3-dichloropropane, 30.7 g of 4-benzyl-6-methyl-1,3-dihydro-furo[3,4-c]-pyridin-7-yl 3-chloropropyl ether, containing a small proportion of 1,3-bis-(4-benzyl-6-methyl-1,3-dihydro-furo[3,4-c]pyridin-7-oxy)-propane, which does not interfere with the subsequent reaction, remain.

(c) 24.2 g (100 millimoles) of 4-benzyl-6-methyl-6-methyl-1,3-dihydro-furo[3,4-c]pyridin-7-ol are suspended in 80 ml of dry dimethylsulfoxide and converted to the sodium salt by adding 3.5 g (120 millimoles) of sodium hydride (85% strength in oil) at 20° C. When the evolution of hydrogen has ceased, 113 g (1 mole) of 1,3-dichloropropane are added dropwise at from 0° to 10° C. and the mixture is stirred for 15 hours at 20° C. The dimethylsulfoxide and excess 1,3-dichloropropane are then distilled off in a high vacuum. The residue is taken up in 250 ml of methylene chloride, and this solution is extracted with twice 50 ml of 10% strength sodium hydroxide solution and washed with 10 ml of water. After distilling off the solvent, 30.7 g of 4-benzyl-6-methyl-1,3-dihydro-furo[3,4-c]-pyridin-7-yl 3-chloropropyl ether containing a small proportion of 1,3-bis-(4-benzyl-6-methyl-1,3-dihydro-furo[3,4-c]-pyridin-7-oxy)-propane remain.

(d) 8.0 g (25 millimoles) of the product obtained as described in (a), (b) or (c) are heated with 15 g (250 millimoles) of isopropylamine for 7 hours at 100° C. in an autoclave. The excess amine is distilled off under reduced pressure. The residue is purified by chromatography on silica gel (ethyl acetate/methanol). The resulting 4-benzyl-6-methyl-1,3-dihydro-furo[3,4-c]pyridin-7-yl 3-isopropylaminopropyl ether is converted, by means of dilute hydrochloric acid, into the bis-hydrochloride, which is recrystallized from isopropanol; 7.8 g, melting point 162° C.

Instead of using chromatography, the crude product can also be purified by extraction with dilute hydrochloric acid. For this purpose, normal hydrochloric acid is added to the solution of the crude product in toluene, whilst shaking, until the aqueous phase has a pH of 6.7. On separating off and concentrating the aqueous phase, 4-benzyl-6-methyl-1,3-dihydro-furo[3,4-c]pyridin-7-yl 3-isopropylaminopropyl ether is obtained as the monohydrochloride, whilst the more weakly basic impurities remain in the toluene phase.

The compounds listed in Table 5 are prepared in a similar manner; in the case of the higher-boiling amines, ie. those boiling above 100°–120° C., the use of an autoclave is superfluous.

TABLE 5

Structure: phenyl-CH₂-[furan-fused pyridine]-O(CH₂)₃N(R⁵)(R⁶) · 2 HCl, with CH₃ on pyridine

| Ex. | NR⁵R⁶ | Melting point, °C. | %N Calc. | %N Found |
|---|---|---|---|---|
| 34 | NHCH(CH₃)₂ | 162 | 6.8 | 6.9 |
| 35 | N(C₂H₅)₂ | 153[a] | 5.3 | 5.5[a] |
| 36 | N(n-C₃H₇)₂ | 184–186 | 6.1 | 6.0 |
| 37 | N(n-C₄H₉)₂ | 178 | 5.8 | 5.7 |
| 38 | NHC₆H₅ | 77–78 | 6.3 | 6.3 |
| 39 | NHC₆H₄-p-OCH₃ | 179 | 5.9 | 5.7 |
| 40 | NHCH₂—C₆H₅ | 214 | 6.1 | 6.2 |
| 41 | NHCH₂CH₂C₆H₅ | 200–201 | 5.9 | 5.7 |
| 42 | 3-methylpiperidin-1-yl | 185 | 6.2 | 6.1 |
| 43 | piperazin-1-yl (N-NH) | 58–60 | 8.8 | 8.6 |

TABLE 5-continued

| Ex. | NR⁵R⁶ | Melting point, °C. | %N Calc. | %N Found |
|---|---|---|---|---|
| 44 | 4-phenylpiperazin-1-yl (N–C₆H₅) | 185–186 | 7.6 | 7.5 |
| 45 | 4-(m-methoxyphenyl)piperazin-1-yl (N–C₆H₄-m-OCH₃) | 209–210 | 7.2 | 7.5 |
| 46 | 4-benzylpiperazin-1-yl (N–CH₂C₆H₅) | 217–218 | 7.4 | 7.5 |

[a] Characterized as the bis-oxalate

EXAMPLES 47 TO 68

Using the method described in Example 34 (a), (b) or (c), 1,4-dichlorobutane, 1,4-dibromo-but-2-ene, 1,5-dichloropentane and 1,5-dichloro-3-methylpentane are used instead of 1,3-dichloropropane to prepare the corresponding ω-haloalkyl ethers, which are then converted by means of an amine, by the method described in Example 34 (d), into the compounds listed in Table 6.

TABLE 6

Structure: phenyl-CH₂-[furan-fused pyridine]-O-A-N(R⁵)(R⁶) · 2 HCl, with CH₃ on pyridine

| Example | A—NR⁵R⁶ | Melting point, °C. | %N Calc. | %N Found |
|---|---|---|---|---|
| 47 | (CH₂)₄NHCH(CH₃)₂ | 198–199 | 6.5 | 6.5 |
| 48 | (CH₂)₄N(CH₃)₂ | 187 | 6.8 | 6.8 |
| 49 | (CH₂)₄N(C₂H₅)₂ | 199–201 | 6.3 | 6.2 |
| 50 | CH₂—CH=CH—CH₂—NHCH(CH₃)₂ | 162–163 | 6.6 | 6.9 |
| 51 | CH₂—CH=CH—CH₂—N(C₂H₅)₂ | 170 | 6.4 | 6.3 |
| 52 | (CH₂)₅NHCH(CH₃)₂ | 173–174 | 6.3 | 6.3 |
| 53 | (CH₂)₅N(CH₃)₂ | 168–169 | 6.5 | 6.5 |
| 54 | (CH₂)₅N(C₂H₅)₂ | 149–151 | 6.2 | 6.2 |
| 55 | (CH₂)₂CH(CH₃)(CH₂)₂NH—CH(CH₃)₂ | 169–170 | 6.2 | 6.2 |
| 56 | (CH₂)₂CH(CH₃)(CH₂)₂N(CH₃)₂ | 140–141 | 6.3 | 6.2 |
| 57 | (CH₂)₂CH(CH₃)(CH₂)₂N(C₂H₅)₂ | 161–162 | 6.0 | 6.0 |
| 58 | (CH₂)₄NHC₂H₅ | 218–220 | 6.8 | 7.0 |
| 59 | (CH₂)₄NH-n-C₃H₇ | 213–214 | 6.6 | 6.8 |
| 60 | (CH₂)₄NH—CH(CH₃)C₂H₅ | 192–193 | 6.3 | 6.5 |
| 61 | (CH₂)₄NH—C(CH₃)₃ | 198–199 | 6.3 | 6.4 |
| 62 | (CH₂)₄NH—CH(CH₃)CH(CH₃)₂ | 161–163 | 6.2 | 6.4 |
| 63 | (CH₂)₄NH—C(CH₃)₂C≡CH | 131–134 | 6.4 | 6.3 |
| 64 | (CH₂)₄N(iso-C₃H₇)₂ | 178–179 | 6.0 | 5.7 |
| 65 | (CH₂)₄NHCH(CH₃)—CH₂OCH₃ | 168–170 | 6.1 | 6.3 |

TABLE 6-continued

[Structure: benzyl-substituted furo-pyridine with O-A-NR⁵R⁶ · 2 HCl]

| Example | A—NR⁵R⁶ | Melting point, °C. | %N Calc. | %N Found |
|---------|---------|-------------------|----------|----------|
| 66 | (CH₂)₄NH—[cyclohexyl-CH₃] | 181–183 | 5.8 | 5.7 |
| 67 | (CH₂)₄NH—[cyclopropyl] | 224 | 6.6 | 6.4 |
| 68 | (CH₂)₄NH(CH₂)₂C(CH₃)₂OH | 209–211 | 5.9 | 5.9 |

EXAMPLE 69

12.1 g (50 millimoles) of 4-benzyl-6-methyl-1,3-dihydro-furo[3,4-c]pyridin-7-ol are suspended in 40 ml of dry dimethylsulfoxide and coverted to the sodium salt by adding 1.75 g (60 millimoles) of sodium hydride (85% strength in oil) at 20° C. When the evolution of hydrogen has ceased, 9.25 g (100 millimoles) of epichlorohydrin are added, the mixture is heated for 1.5 hours at 60° C., 30 g (0.5 mole) of isopropylamine are added and the batch is heated at 100° C. in an autoclave for 2.5 hours. Excess amine and dimethylsulfoxide are then stripped off under reduced pressure. The residue is taken up in methylene chloride, the solution is washed with 10% strength sodium hydroxide solution and water and is dried, and the solvent is again stripped off. The residue is purified by chromatography on silica gel (ethyl acetate/methanol). After conversion to the hydrochloride, and recrystallization from acetonitrile, 10.5 g of 4-benzyl-6-methyl-1,3-dihydrofuro[3,4-c]pyridin-7-yl 2-hydroxy-3-isopropylaminopropyl ether hydrochloride are obtained; melting point 152°–154° C.

The compounds listed in Table 7 are prepared in a similar manner.

TABLE 7

[Structure: pyridine with R¹, R², R³, R⁴ substituents and —OCH₂—CH(OH)—CH₂—NR⁵R⁶ · 2 HCl]

| Example | R¹ | R² | R³ | R⁴ | NR⁵R⁶ | Melting point, °C. | %N Calc. | %N Found |
|---------|-----|-----|-----|-----|--------|-------------------|----------|----------|
| 69ᵃ | CH₃ | CH₂OCH₂ | | C₆H₅CH₂ | NHCH(CH₃)₂ | 152–154 | 7.1 | 7.0 |
| 70 | CH₃ | CH₂OCH₂ | | C₆H₅ | NHCH(CH₃)₂ | 194 | 6.7 | 6.6 |
| 71 | CH₃ | CH₂OCH₂ | | H | NHCH(CH₃)₂ | 162ᵇ | 6.3 | 6.0ᵇ |
| 72 | CH₃ | H | | H | C₆H₅CH₂ NHCH(CH₃)₂ | 138–140 | 7.2 | 6.9ᵇ |
| 73 | CH₃ | CH₂OCH₂ | | C₆H₅CH₂ | N(CH₃)₂ | 216–218 | 6.7 | 6.7 |
| 74 | CH₃ | CH₂OCH₂ | | C₆H₅CH₂ | N(C₂H₅)₂ | 141–142 | 6.3 | 6.0 |
| 75ᵃ | CH₃ | CH₂OCH₂ | | C₆H₅CH₂ | N(CH(CH₃)₂)₂ | 66–68 | 5.9 | 5.7 |
| 76 | CH₃ | CH₂OCH₂ | | C₆H₅CH₂ | [piperidinyl] | 202–204 | 6.2 | 6.0 |
| 77 | CH₃ | CH₂OCH₂ | | C₆H₅CH₂ | NH(CH₂)₃—N(CH₃)₂ | 141–142 | 8.3 | 8.1 |
| 78 | CH₃ | CH₂OCH₂ | | C₆H₅CH₂ | [4-phenyl-4-hydroxypiperidinyl] | 210–212 | 5.1 | 4.8 |

Notes on Table 7:
ᵃMonohydrochloride
ᵇCharacterized as the oxalate
ᶜReacted by heating with diisopropylamine for 6 hours at 125° C.

EXAMPLE 79

4,6-Dibenzyl-1,3-dihydro-furo[3,4-c]pyridin-7-ol is converted to the δ-chlorobutyl ether by reaction with 1,4-dichlorobutane, using the method of Example 34 (a). This ether is then converted, by the method of Example 34 (d), into 4,6-dibenzyl-1,3-dihydro-furo[3,4-c]pyridin-7-yl-δ-isopropylaminobutyl ether bis-hydrochloride, which is a glassy product. N determination: calculated 5.6%, found 5.5%.

EXAMPLE 80

2-Methyl-4,5-dicarbethoxy-6-benzyl-pyridin-3-ol is converted to the δ-chlorobutyl ether by reaction with 1,4-dichlorobutane, using the method of Example 34 (a). This ether is then converted, by the method of Example 34 (d), into 2-methyl-4,5-dicarbethoxy-6-benzyl-pyridin-3-yl δ-isopropylaminobutyl ether bis-hydrochloride, melting point 165°–166° C. N determination: calculated 5.3%, found 5.4%.

EXAMPLES 81 TO 85

Using the method of Example 34 (a), 1,4-dichlorobutane is reacted, instead of 1,3-dichloropropane, to give the corresponding 4-chlorobutyl ethers, which are then reacted with isopropylamine, by the method of Example 34 (d), to give the compounds listed in Table 8.

TABLE 8

Structure: $R^4$-substituted furo-pyridine with $CH_3$ on N=, and $-O-(CH_2)_4NHCH(CH_3)_2 \cdot HCl$

| Example | $R^4$ | Melting point, °C. | % N Calc. | % N Found |
|---|---|---|---|---|
| 81 | 4-Cl—$C_6H_4CH_2$ | 123 | 6.6 | 6.8 |
| 82 | 3-$CH_3$—$C_6H_4CH_2$ | 148 | 6.9 | 7.1 |
| 83 | 3-$CF_3$—$C_6H_4CH_2$ | 146 | 6.1 | 6.0 |
| 84 | $C_6H_5$ | 192 | 7.4 | 7.5 |
| 85 | thienyl-$CH_2$ | 117 | 7.0 | 6.7 |

EXAMPLE 86

Hydrolysis of 2-methyl-4-carbethoxy-6-benzyl-pyridin-3-yl 3-dimethylaminopropyl ether (Example 19) with methanolic potassium hydroxide solution at 60° C. gives 2-methyl-4-carboxy-6-benzyl-pyridin-3-yl 3-dimethylaminopropyl ether, of melting point 157° C. N determination: calculated 8.5%, found 8.6%.

Examples of formulations which are prepared in the conventional manner:

| Tablets: | |
|---|---|
| (a) An active ingredient of the formula I | 5 mg |
| Lactose | 200 mg |
| Methylcellulose | 15 mg |
| Corn starch | 50 mg |
| Talc | 11 mg |
| Magnesium stearate | 4 mg |
| | 285 mg |
| (b) An active ingredient of the formula I | 20 mg |
| Lactose | 178 mg |
| Avicel | 80 mg |
| Polywachs 6,000 | 20 mg |
| Magnesium stearate | 2 mg |
| | 300 mg |
| (c) An active ingredient of the formula I | 50 mg |
| Polyvinylpyrrolidone (mean molecular weight 25,000) | 170 mg |
| Polyethylene glycol (mean molecular weight 4,000) | 14 mg |
| Hydroxypropylmethylcellulose | 40 mg |
| Talc | 4 mg |
| Magnesium stearate | 2 mg |
| | 280 mg |

The active ingredient is moistened with a 10% strength aqueous solution of polyvinylpyrrolidone, forced through a sieve having a mesh width of 1.0 mm, and dried at 50° C. These granules are mixed with polyethylene glycol (mean molecular weight 4,000), hydroxypropylmethylcellulose, talc and magnesium stearate, and the mixture is pressed to give tablets each weighing 280 mg.

| 2. Example of dragees: | |
|---|---|
| An active ingredient of the formula I | 60 mg |
| Lactose | 90 mg |
| Corn starch | 60 mg |
| Polyvinylpyrrolidone | 6 mg |
| Magnesium stearate | 1 mg |
| | 217 mg |

The mixture of the active ingredient with lactose and corn starch is treated with an 8% strength aqueous solution of the polyvinylpyrrolidone and granulated by passing through a 1.5 mm sieve; the granules are dried at 50° C. and forced through a 1.0 mm sieve. The granules thus obtained are mixed with magnesium stearate and the mixture is pressed to form dragee cores. These are coated in the conventional manner with a coating essentially consisting of sugar and talc.

| 3. Capsule formulation: | |
|---|---|
| An active ingredient of the formula I | 5.0 mg |
| Magnesium stearate | 2.0 mg |
| Lactose | 19.3 mg |
| 4. Injection solution: | |
| An active ingredient of the formula I | 10 mg |
| Sodium chloride | 9 mg |
| Distilled water to make up to 1.0 ml | |

We claim:
1. A pyridinyl aminoalkyl ether of the Formula I

Formula I: pyridine ring with substituents $R^1$, $R^2$, $R^3$, $R^4$ and $-O-A-N(R^5)(R^6)$ wherein
$R^1$ is hydrogen, alkyl of 1 to 5 carbon atoms or benzyl;
$R^2$ and $R^3$ are identical and each is methyl substituted by hydroxyl, alkoxy, alkylthio or dialkylamino, alkyl in each case being of 1 to 4 carbon atoms, or alkoxycarbonyl when alkyl is of 1 to 4 carbon atoms, or $R^2$ and $R^3$ together are —CH$_2$—B—CH$_2$— and form a 5-membered ring with the carbon atoms by which they are linked, B being methylene, oxygen, sulfur or nitrogen, and the nitrogen being unsubstituted or substituted by alkyl of 1 to 5 carbon atoms, or phenyl;

$R^4$ is phenyl, benzyl or α- or β-phenylethyl, the phenyl rings being unsubstituted or substituted by hydroxyl, halogen, alkyl or alkoxy, alkyl being of 1 to 3 carbon atoms, and A is straight-chain or branched alkylene of 2 to 8 carbon atoms, which is saturated or unsaturated, or A is additionally 2-hydroxy-1,3-propylene, when $R^2$ and $R^3$ are 2-oxatrimethylene, $R^5$ is hydrogen, or alkyl of 1 to 6 carbon atoms which is unsubstituted or substituted by hydroxyl, alkoxy, alkylthio, alkylamino or dialkylamino, where alkyl is in each case of 1 to 4 carbon atoms, or by phenoxy or phenyl, the phenyl rings being unsubstituted or additionally substituted by alkyl or alkoxy of 1 to 3 carbon atoms, or is alkenyl or alkynyl of 3 to 6 carbon atoms, cycloalkyl, where the ring is of 3 to 8 carbon atoms and which is unsubstituted or substituted by alkyl of 1 to 3 carbon atoms, or phenyl, which is unsubstituted or substituted by alkyl or alkoxy, alkyl in each case being of 1 to 3 carbon atoms, $R^6$ is hydrogen or alkyl of 1 to 6 carbon atoms, or $R^5$ and $R^6$ together with the N-atom are a 4-membered to 8-membered ring which may or may not contain a further oxygen, nitrogen or sulfur atom and is unsubstituted or substituted by alkyl of 1 to 3 carbon atoms, cycloalkyl, where the ring is of 3 to 8 carbon atoms, hydroxyl, alkoxy of 1 to 4 carbon atoms or phenyl or phenylalkyl of 7 to 9 carbon atoms, the phenyl rings being unsubstituted or substituted by alkyl or alkoxy of 1 to 3 carbon atoms, and its physiologically acceptable addition salts with acids.

2. A compound as set forth in claim 1, where $R^1$ is hydrogen, alkyl of 1 to 4 carbon atoms or benzyl, $R^2$ and $R^3$ are alkoxycarbonyl, alkyl being of 1 to 3 carbon atoms, or $R^2$ and $R^3$ together are trimethylene, 2-oxatrimethylene or 2-methylaza-trimethylene and $R^4$ is benzyl, A is alkylene of 3 to 5 carbon atoms which is unsubstituted or methyl-substituted, or A is 2-hydroxy-1,3-propylene when $R^2$ and $R^3$ are 2-oxatrimethylene, and $R^5$ is hydrogen or alkyl of 1 to 5 carbon atoms, which is unsubstituted or hydroxyl-substituted, or is benzyl, and $R^6$ is hydrogen or alkyl of 1 to 4 carbon atoms, or $R^5$ and $R^6$ together with the nitrogen are a pyrrolidine, piperidine or piperazine ring and its physiologically acceptable addition salts with acids.

3. A pyridinyl aminoalkyl ether as set forth in claim 1 wherein the pyridinyl radical is selected from the group consisting of 4-benzyl-1,3-dihydro-furo[3,4-c]pyridin-7-yl, 4-benzyl-6-methyl-1,3-dihydrofuro[3,4-c]pyridin-7-yl, 4-benzyl-6-ethyl-1,3-dihydrofuro[3,4-c]pyridin-7-yl, 4-benzyl-6-isobutyl-1,3-dihydrofuro[3,4-c]pyridin-7-yl, 4,6-dibenzyl-1,3-dihydrofuro[3,4-c]pyridin-7-yl, 1-benzyl-3-methyl-6,7-dihydro-5-H-2-pyrindin-4-yl, 4-benzyl-2,6-dimethyl-2,3-dihydro-1-H-pyrrolo[3,4-c]pyridin-7-yl, 2-methyl-4,5-dicarbomethoxy-6-benzyl-pyridin-3-yl and 2-methyl-4,5-dicarboethoxy-6-benzyl-pyridin-3-yl.

4. 6-Benzyl-2-methyl-4,5-dicarbethoxy-pyridin-3-yl 3-dimethylaminopropyl ether.

5. 6-Benzyl-2-methyl-4,5-dicarbomethoxy-pyridin-3-yl 3-dimethylaminopropyl ether.

6. 4,6-Dibenzyl-1,3-dihydro-furo[3,4-c]pyridin-7-yl 3-dimethylaminopropyl ether.

7. 4-Benzyl-6-methyl-1,3-dihydro-furo[3,4-c]pyridin-7-yl 3-isopropylaminopropyl ether.

8. 4-Benzyl-6-methyl-1,3-dihydro-furo[3,4-c]pyridin-7-yl 4-isopropylaminobutyl ether.

9. 4-Benzyl-6-methyl-1,3-dihydro-furo[3,4-c]pyridin-7-yl 5-isopropylamino-3-methylpentyl ether.

10. 4-Benzyl-6-methyl-1,3-dihydro-furo[3,4-c]pyridin-7-yl 5-diethylamino-3-methylpentyl ether.

11. 4-Benzyl-6-methyl-1,3-dihydro-furo[3,4-c]pyridin-7-yl 4-tert.-butylamino-butyl ether.

12. A therapeutic agent which contains a therapeutically effective amount of a compound as set forth in claim 1 or one of its physiologically acceptable addition salts with an acid, as the active ingredient, in addition to conventional excipients and diluents.

13. A therapeutic agent, which contains a therapeutically effective amount of a compound as set forth in claim 1 where $R^1$ is hydrogen, alkyl of 1 to 4 carbon atoms or benzyl, $R^2$ and $R^3$ are alkoxycarbonyl, alkyl being of 1 to 3 carbon atoms, or $R^2$ and $R^3$ together are trimethylene, 2-oxatrimethylene or 2-methylazatrimethylene and $R^4$ is benzyl, A is alkylene of 3 to 5 carbon atoms which is unsubstituted or methylsubstituted, or is 2-hydroxy-1,3-propylene, and $R^5$ is hydrogen or alkyl of 1 to 5 carbon atoms, which is unsubstituted or hydroxyl-substituted, or is benzyl, and $R^6$ is hydrogen or alkyl of 1 to 4 carbon atoms, or $R^5$ and $R^6$ together with the nitrogen are a pyrrolidine, piperidine or piperazine ring or one of its physiologically acceptable addition salts with an acid, as the active ingredient, in addition to conventional excipients and diluents.

14. A process for treating cardiac arrhythmias which comprises:
   administering to a patient to be treated an effective amount of a compound as set forth in claim 1, said compound being mixed with a pharmaceutically acceptable carrier, said compound being administered in single dosage amounts of from 5 to 100 mg.

* * * * *